(12) United States Patent
Olivera et al.

(10) Patent No.: US 6,969,032 B2
(45) Date of Patent: Nov. 29, 2005

(54) INFUSION FLUID CONTAINER SUPPORT

(75) Inventors: Argelio M. Olivera, Los Alamitos, CA (US); Stanley C. Polski, Fullerton, CA (US)

(73) Assignee: Alcon, Inc., Hunenberg (CH)

( * ) Notice: Subject to any disclaimer, the term of this patent is extended or adjusted under 35 U.S.C. 154(b) by 301 days.

(21) Appl. No.: 10/318,825

(22) Filed: Dec. 13, 2002

(65) Prior Publication Data

US 2004/0116846 A1 Jun. 17, 2004

(51) Int. Cl.⁷ .............................................. F16M 13/00
(52) U.S. Cl. .................................................. 248/176.1
(58) Field of Search ............................ 606/107.1, 130, 606/166, 167; 604/22, 30, 36, 80; 248/125.1, 176.1, 176.3, 333, 550

(56) References Cited

U.S. PATENT DOCUMENTS

| 3,898,555 A | 8/1975 | Tellerman |
| 4,607,897 A | 8/1986 | Schwartz |
| 5,007,688 A | 4/1991 | Bayerlein et al. |
| 5,112,019 A | 5/1992 | Metzler et al. |
| 5,857,685 A | 1/1999 | Phillips et al. |
| 6,022,088 A | 2/2000 | Metzler |
| 6,251,113 B1 * | 6/2001 | Appelbaum et al. ........ 606/107 |

OTHER PUBLICATIONS

CooperVision Surgical brochure for the Cavitron/Kelmar® Phaco–Emulsifier® Aspirator, Model 9001, Copyright 1985, 2 pages.

* cited by examiner

*Primary Examiner*—Kevin C. Sirmons
(74) *Attorney, Agent, or Firm*—Jeffrey S. Schira (57) ABSTRACT

Apparatus and methods for use in ophthalmic surgery in which a container for fluid is connected to a line through which fluid flows to a surgical handpiece for the irrigation of a patient's eye are provided. A sensor emits a magnetic field and a detector causes another magnetic field to be generated. The interaction of the two magnetic fields causes a pulse to be generated. Based on the timing of the generated pulse, the apparatus or method determines the absolute position of the support coupled to the container and adjusts the height of the support. Circuitry is also provided to prevent changes in height of the support by preventing supply of drive currents and by applying a hold current or by generating an electro motive force.

40 Claims, 11 Drawing Sheets

INFUSION FLUID CONTAINER SUPPORT

BACKGROUND OF THE INVENTION

The present invention relates generally to an apparatus for ophthalmic surgery, and more particularly to an apparatus for use in ophthalmic surgery with controls to adjust and determine the height of a support coupled to a container from which fluid flows with a desired pressure to a surgical handpiece for the irrigation of a patient's eye.

Ophthalmic surgery is useful in treating various conditions relating to the eyes. One condition which may be alleviated by surgery is cataracts, which are sometimes described as clouding of the eyes. As old cells die, they accumulate within a capsule containing the lens of the eye. This accumulation of dead cells causes an occlusion of the lens, i.e., a cataract.

There are many surgical available techniques to alleviate or treat cataracts. In some techniques, a solution or fluid is used to irrigate the eye. Operating and controlling a system to deliver or provide the solution can be an issue, and the systems may be complex. In particular, initial calibrations may be required in order to regulate the supply of the solution. Performing these initial calibrations may slow operation times. Additionally, at times, it is useful to identify the position of a container for the solution to regulate fluid pressure and/or an amount of fluid being supplied.

SUMMARY OF THE INVENTION

The present invention provides an apparatus for use in ophthalmic surgery in which a container for fluid is connected to a line through which fluid flows to a surgical handpiece for the irrigation of a patient's eye. The apparatus may comprise a base, a support, an encoder and a controller. The support extends from the base and is coupled to the container from which fluid is supplied to the surgical handpiece. The encoder can be arranged to determine the absolute position of the support and the controller can be arranged to adjust the height of the support based on the absolute position determined, whereby accurate determination and adjustment of the height of the support ensures that the fluid from the container flows with a desired pressure to the surgical handpiece and into the patient's eye.

In one aspect of the invention, an apparatus for use in ophthalmic surgery is provided in which a container for fluid is connected to a line through which fluid flows to a surgical handpiece for the irrigation of a patient's eye. The apparatus comprises means for supporting the container, such as a pole and/or hanger, from which fluid is supplied to the surgical handpiece, means for determining the absolute position of the means for supporting the container with reference to a base, such as a magnet, signal conditioner and a waveguide, and means for adjusting the height of the support based on the absolute position determined, such as a control board and/or motor, whereby accurate determination and adjustment of the height of the support ensures that the fluid from the container flows with a desired pressure to the surgical handpiece and into the patient's eye. A further aspect of the invention provides a means for emitting a first magnetic field, such as a magnet, proximate the container and a means for emitting a second magnetic field to interact with the first magnetic field, such as a signal conditioner and waveguide.

In another aspect of the invention, an apparatus is provided for use in ophthalmic surgery in which a container for fluid is connected to a line through which fluid flows to a surgical handpiece for the irrigation of a patient's eye. The apparatus comprises a support, a motor and circuitry. The support is coupled to the container from which fluid is supplied to the surgical handpiece. The motor generates an electro motive force and the circuitry is arranged to prevent vertical movement of the support based on the force generated, whereby the prevention of vertical movement of the support ensures that irrigation fluid from the container flows with a desired pressure to the surgical handpiece and into the patient's eye.

In still another aspect of the invention, an apparatus is provided for use in ophthalmic surgery in which a container for fluid is connected to a line through which fluid flows to a surgical handpiece for the irrigation of a patient's eye. The apparatus comprises a support, a motor and circuitry. The support is coupled to the container from which fluid is supplied to the surgical handpiece. The motor is arranged to vertically move the support and the circuitry is arranged to supply a current to the motor to prevent vertical movement of the support, the current supplied having a magnitude that is proportional to a force applied to the motor by the weight of the support, whereby the prevention of vertical movement of the support ensures that fluid from the container flows with a desired pressure to the surgical handpiece and into the patient's eye.

In a further aspect of the invention, an apparatus for use in ophthalmic surgery is provided in which a container for fluid is connected to a line through which fluid flows to a surgical handpiece for the irrigation of a patient's eye. The apparatus comprises a pole for supporting a container, a magnet for generating a first magnetic field and a carrier housing the magnet and coupled to a portion of the support. The apparatus also includes a waveguide proximate the pole containing magnetostrictive strain material and a signal conditioner arranged to cause current to flow through the waveguide to emit a second magnetic field and further arranged to detect a pulse generated from the interaction of the first magnetic field and a second magnetic field. The motor can have windings and can be arranged to adjust the height of the pole and the carrier. A control board is also arranged to determine the height of the pole based on a time interval between the flow of current to the detection of the pulse by the signal conditioner and further arranged to energize the motor to adjust the length of the pole. In addition, transistor drivers are arranged to supply drive currents to the windings of the motor and transistor switches are arranged to deactivate the drivers and to supply a current to one of the windings to prevent movement of the motor, whereby accurate determination and adjustment of the height of the support ensures that the fluid from the container flows with a desired pressure to the surgical handpiece and into the patient's eye.

Another aspect of the invention is a method for use in ophthalmic surgery in which a container for fluid is connected to a line through which fluid flows to a surgical handpiece for the irrigation of a patient's eye. The method comprises attaching to a support the container from which fluid is supplied to the surgical handpiece, supplying a current, preventing change of the height of the support by adjusting the current supplied, the current supplied having a magnitude that is proportional to the force exerted by the weight of the support, whereby the prevention of the change of height of the support ensures that fluid from the container flows with a desired pressure to the surgical handpiece and into the patient's eye.

In yet another aspect of the invention, a method for use in ophthalmic surgery is provided in which a container for fluid is connected to a line through which fluid flows to a surgical handpiece for the irrigation of a patient's eye. The method attaches to a support the container from which fluid is supplied to the surgical handpiece, detects the absolute position of the support with reference to a base and adjusts the height of the support based on the absolute position detected, whereby accurate determination and adjustment of the height of the support ensures that the fluid from the container flows with a desired pressure to the surgical handpiece and into the patient's eye.

In a further aspect of the invention, a method for use in ophthalmic surgery is provided in which a container for fluid is connected to a line through which fluid flows to a surgical handpiece for the irrigation of a patient's eye. The method comprises attaching to a support the container from which fluid is supplied to the surgical handpiece, generating an electro motive force and preventing change of the height of the support based on the force generated, whereby the prevention of the change of height of the support ensures that fluid from the container flows with a desired pressure to the surgical handpiece and into the patient's eye.

Many of the attendant features of this invention will be more readily appreciated as the same becomes better understood by reference to the following detailed description and considered in connection with the accompanying drawings.

DETAILED DESCRIPTION

Figure 1:
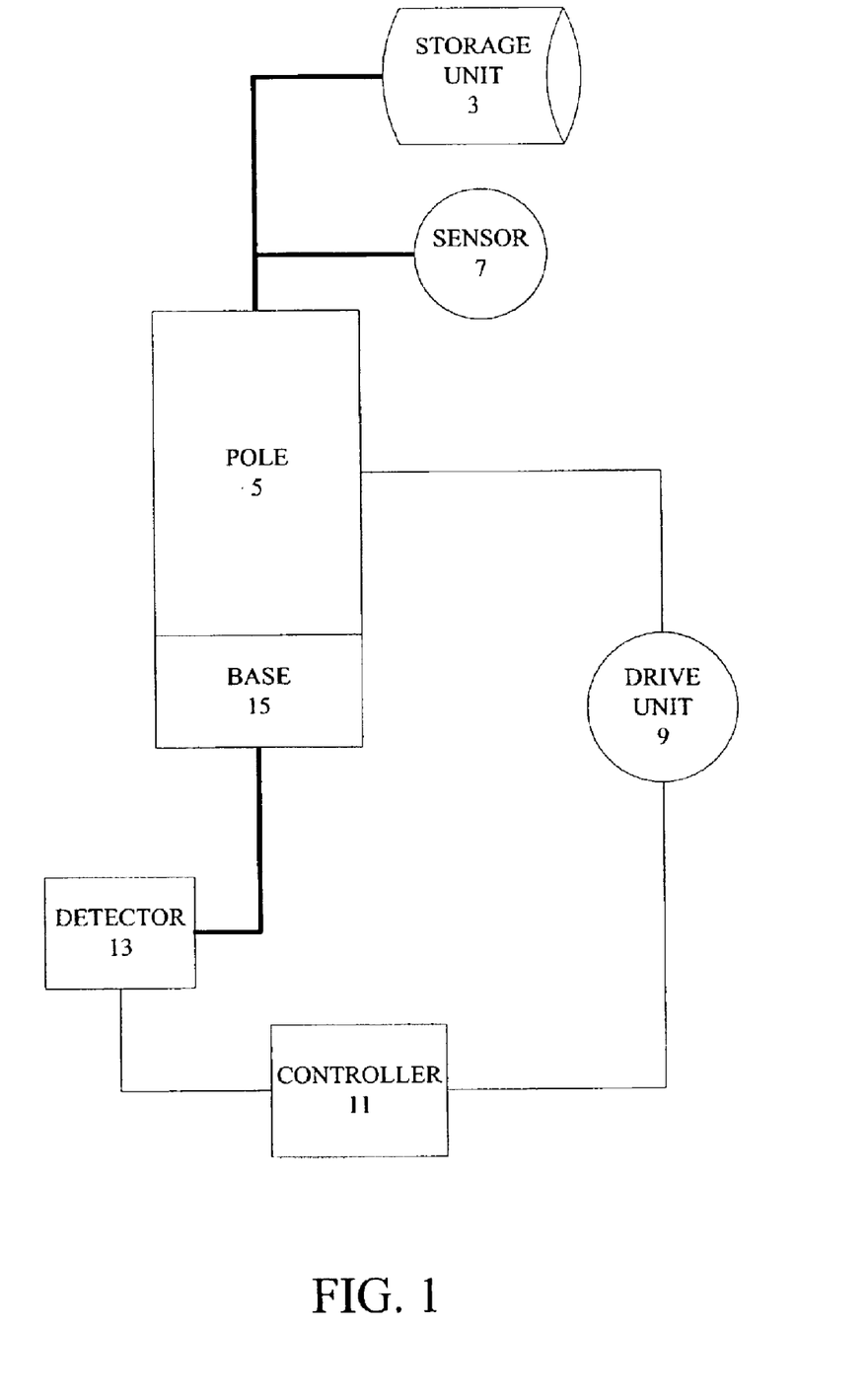
FIG. 1 is a block diagram of an apparatus for use in ophthalmic surgery.

A telescoping pole 5, shown schematically in FIG. 1, forms a height adjustable support. In one embodiment, the pole is attached to a base 15, with the length of the pole adjustable. A lower section of the pole is adapted to be mounted to a base, such as on a console or cart that can be placed on the floor. An upper section of the pole extends in a telescoping manner from the lower section, and the amount of extension is selectable. A drive unit 9 is coupled to the pole 5 and is configured to adjust the height of the pole. For example, the drive unit, when actuated, engages the lower section of the pole. The lower section of the pole engages the upper section of the pole to cause the upper section to extend from the lower section of the pole.

A storage unit 3 is also coupled to the pole 5. The storage unit comprises one or more containers, such as bottles or bags, holding a fluid such as a saline solution. In some embodiments, these containers are suspended from the top of pole. A pole, such as pole 5 and other poles discussed herein, can be a means for supporting the container from which fluid is supplied. Fluid from the container is used to irrigate a patient's eye (not shown). The fluid pressure at the eye is dependent on the height of the pole from which the solution is suspended relative to the patient.

A detector 13 and a sensor 7 provide a signal indicative of the relative vertical position of the storage unit 3 and the base 15. The detector 13 is fixed in position relative to the base 15. The sensor 7, although movable, is fixed in position relative to the pole 5. In some embodiments placement of the detector and sensor are reversed. Height adjustment of the pole with respect to the base results in relative movement of the sensor with respect to the detector.

A controller 11, coupled to the drive unit 9, receives from the detector a signal indicative of the distance between the sensor and the detector, and thus the relative height of the storage unit. The controller 11 causes the drive unit 9 to adjust the pole 5 based on information from the detector 13. As such, the sensor and detector together act as an absolute encoder that provides an absolute position of the storage unit or a portion of the pole. The absolute position is defined as the distance between the detector 13 and the sensor 7 measured along the pole. The determination of the absolute position may be accomplished with reference to a predetermined offset or location, such as an offset of distance between the detector and the base and/or an offset of distance between the sensor and the storage unit. The absolute position is also determined without determining previous locations of the pole 5 or actuation of the drive unit 9.

In other words, using the number of turns the drive unit 9 rotates in relation to the previous position of the drive unit, an approximation of the height of the pole 5 could be determined. However, by directly measuring an absolute position, the actual distance between two points on the pole, one fixed, e.g., the detector 13, and the other adjustable, e.g., the sensor 7, the height of the pole is quickly and reliably determined. Therefore, recording a previous position of the drive unit or calibrating a drive unit to relate the rotational movement of the drive unit to the translational movement of the pole, which may be time consuming, is not necessary.

In some embodiments, the controller 11 determines the height of the pole 5 or the amount of fluid pressure desired or expected by a user, such as a surgeon. As such, based on the absolute position determined and the height expected, the controller 11 causes the drive unit 9 to extend or retract the pole 5 in a vertical direction, e.g., up or down.

In one embodiment, the detector 13 generates a current pulse. The current pulse travels through a waveguide (not shown) coupled parallel to the pole 5. As such, a traveling magnetic field is generated by the current pulse, with the magnetic field traveling through the waveguide. The sensor 7 is configured to generate another magnetic field. The traveling magnetic field interacts with the other magnetic field as the traveling field moves along the waveguide. The interaction with the two magnetic fields results in a strain pulse that is received or detected by the detector 13. A detector 13 can be a means for emitting a first magnetic field proximate the support means, and a sensor 7 can be a means for emitting a second magnetic field to interact with the first magnetic field. In one embodiment, the strain pulse induces current, a magnetic field, or mechanical force along the waveguide.

The detector 13, in one embodiment, identifies the induced current along the waveguide using a transistor or inductor to determine receipt of the strain pulse. The amount of time from the initiation of the current pulse from the detector to the receipt of the strain pulse is proportional to the distance between the detector 13 and the sensor 7. Based on the time elapsed from transmission of the current pulse to receipt of the strain pulse, the controller 11 determines the distance between the sensor and the detector. A controller 11 can be a means for measuring a time between when the second magnetic field is emitted to when a pulse reaches a means for emitting the second magnetic field, such as a sensor. One example of an absolute encoder, e.g., the detector 13 and sensor 7, is described in U.S. Pat. No. 3,898,555, the disclosure of which is hereby incorporated by reference. Therefore, a position or height of the pole can be identified quickly and reliably without approximations or initial calibrations.

Figure 2:
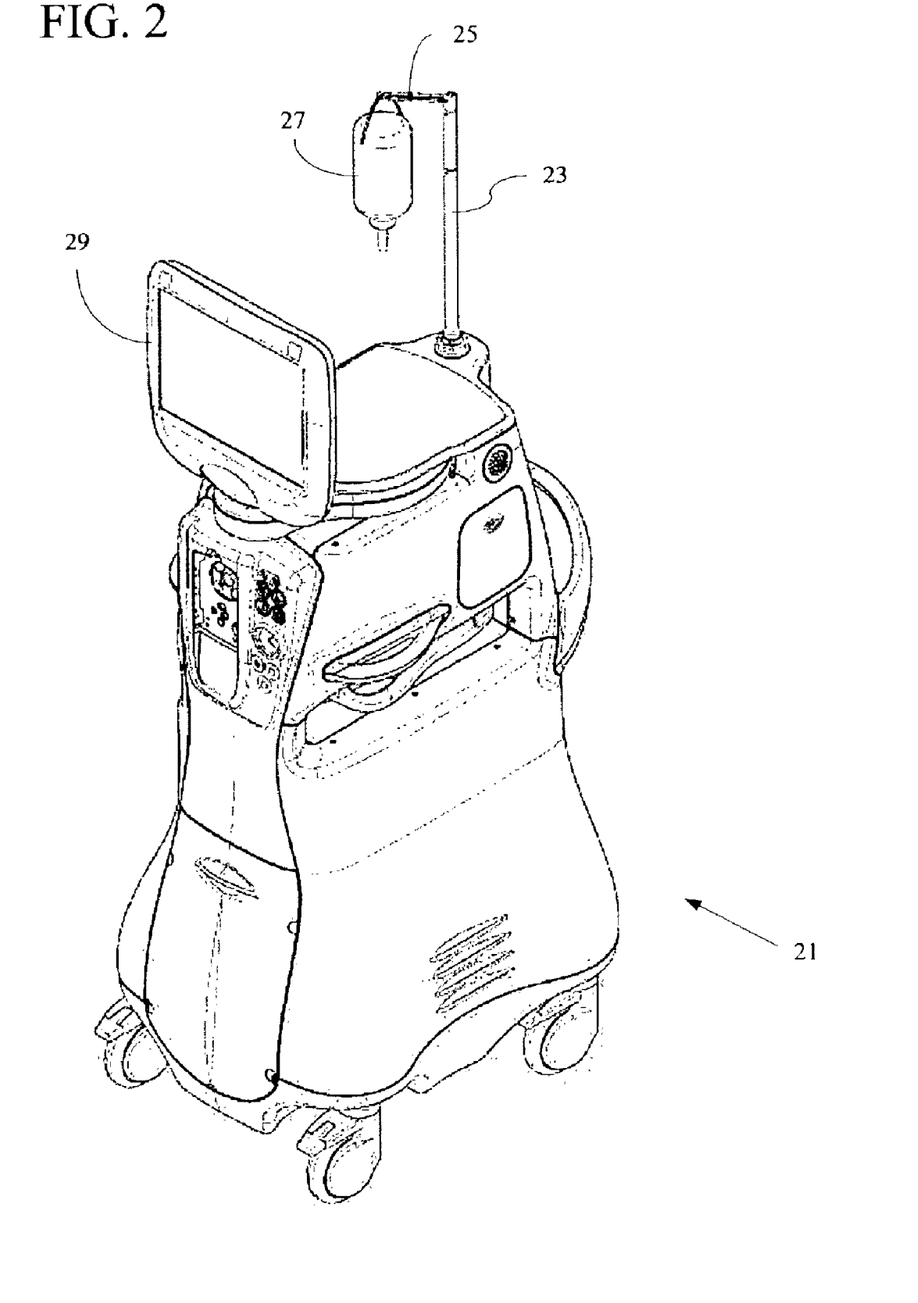
FIG. 2 is a perspective view of an apparatus for use in ophthalmic surgery.

A pole 23 is mounted on a console 21, as shown in FIG. 2, so as to extend upwardly 6 from the console. The console also houses a motor (not shown) used to move or adjust the length of telescoping pole 23. The pole 23 extends upward from the console 21. A hanger 25 is attached to the pole near the top and supports a container 27. A pole or a hanger 25 can be a means for supporting the container. The container is filled with, for example, a saline solution. Fluid from the container is delivered to a surgical handpiece for administration to the eye of a patient.

The console 21, in one embodiment, also houses and/or is connected to consumables, input devices, medical instruments and other devices or components for performing medical or surgical procedures. A monitor 29 is also connected to and mounted on the console 21 to provide feedback, graphical and/or textual information, regarding the surgical procedure and other status data, including the height of the pole. Through the monitor and a touch screen on the monitor or through other input devices, the user can monitor and adjust the height of the pole to adjust, for example, the flow rate of the fluid from the container and the pressure at the eye.

Figure 3:
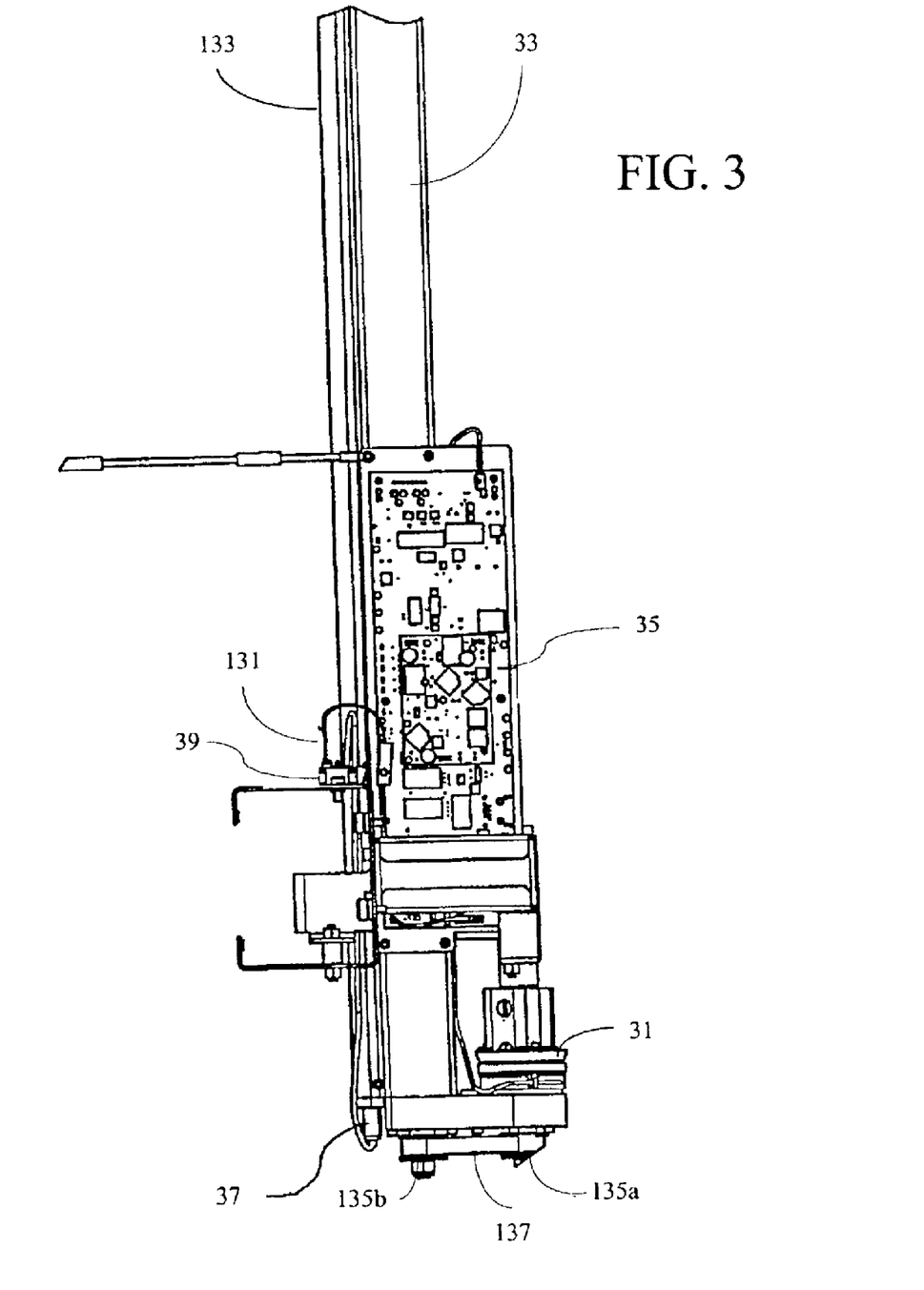
FIG. 3 is a side view of an apparatus for use in ophthalmic surgery.

FIG. 3 illustrates another apparatus in accordance with the invention, for use in ophthalmic surgery. A motor and/or a control board can be a means for adjusting the height of a support. More particularly, this apparatus includes a pole 33. A motor 31 is coupled to the pole 33, with the motor configured to adjust the height of the pole in a telescoping manner. The motor 31 is connected to pulleys 135a, b and a pulley belt 137. When energized, the motor 31 rotates which causes a shall (not shown) to rotate. On the end of the shaft not attached to the motor, the pulley 135a is attached. The pulley 135a therefore also rotates in a corresponding manner as the motor rotates. Pulley belt 137 couples pulley 135a to pulley 135b which transfers the rotational motion of pulley 135a to pulley 135b. Thus, as pulley 135a rotates, pulley 135b also rotates. The pulley 135b is coupled to the pole 33 via a lead screw (not visible). As the lead screw is rotated by pulley 135b, the screw threads engage the pole causing the pole's height to be adjusted. Therefore, depending on the motor turning clockwise, for example, the pole extends and with the motor turning counter clockwise, the pole is retracted.

A control board 35 is also coupled to the pole 33 and, as illustrated, adjacent to the motor 31. The control board receives a signal from a detector head 37. The detector head is coupled to a detector controller 39 via input/output cables 131. In one embodiment, the detector controller and the control board are a single component. A waveguide (not shown) extends parallel to the pole, with the waveguide covered by a support assembly 133. Also covered by the support assembly is a magnet (not shown) which is movable along the waveguide. The support assembly prevents the magnet and/or waveguide from interfering with other components and vice versa.

Figure 4:
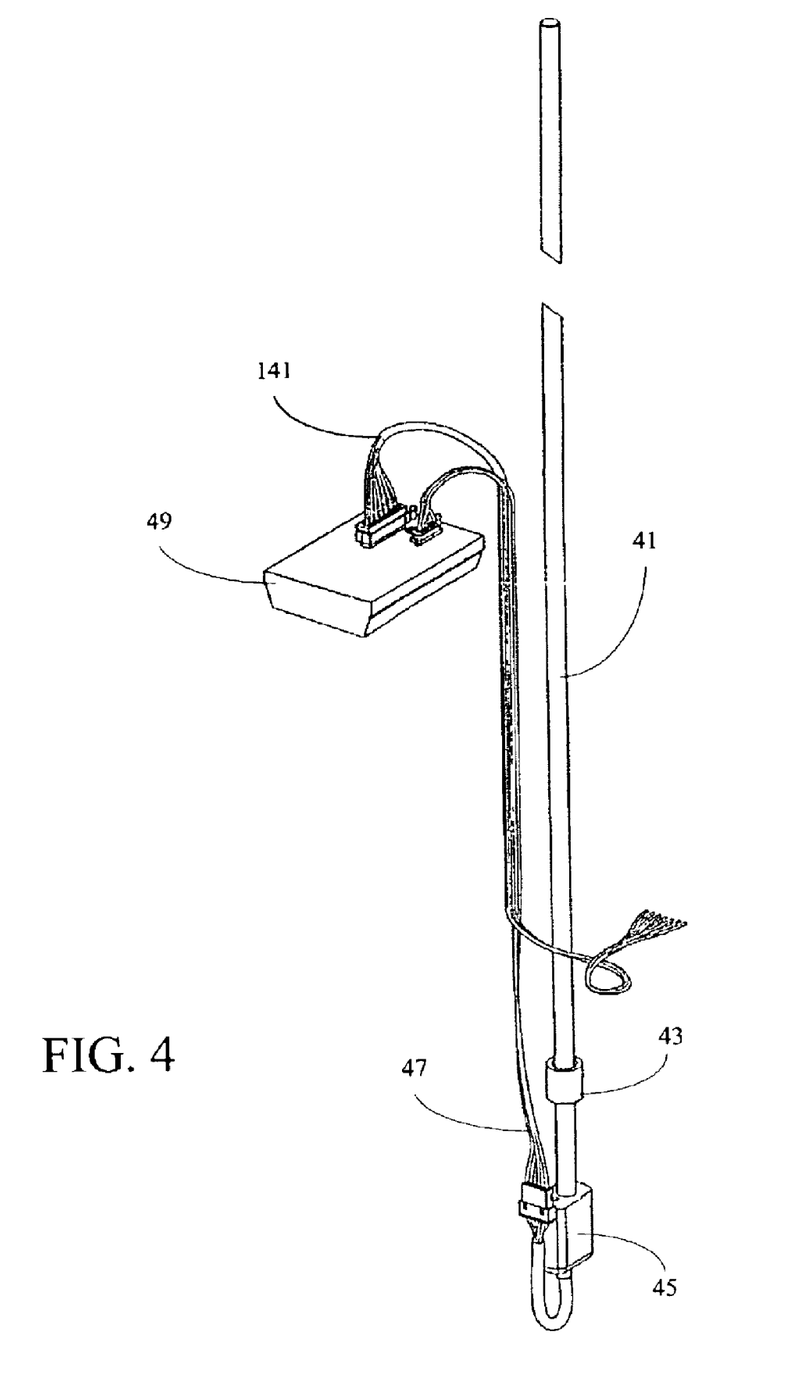
FIG. 4 is a perspective view of a portion of a partially disassembled sensor assembly for an apparatus for use in ophthalmic surgery to supply liquid from a container for the liquid.

A detector head 45 is coupled to one end of the waveguide 41, shown in FIG. 4. A magnet 43 substantially surrounds the waveguide and is moveable longitudinally along the waveguide. The detector head 45 is coupled to a signal conditioner or detector controller 49 via input cables 47. The detector controller 49 is also coupled to a control unit (not shown) via output cables 141. A magnet 43, a signal conditioner or detector controller 49, and a waveguide 41 can be a means for determining the absolute position of the support for the container for fluid.

A current pulse generated by the detector head 45 causes a magnetic wave to travel through the waveguide 41. This wave interacts with a magnetic field generated by the magnet 43 to cause a strain pulse to travel back toward the detector head 45. The detector head senses the strain pulse and provides a return signal to the detector controller 49. In one embodiment, the detector controller and the control unit are integrated and output cables 141 are therefore not utilized.

Figure 5:
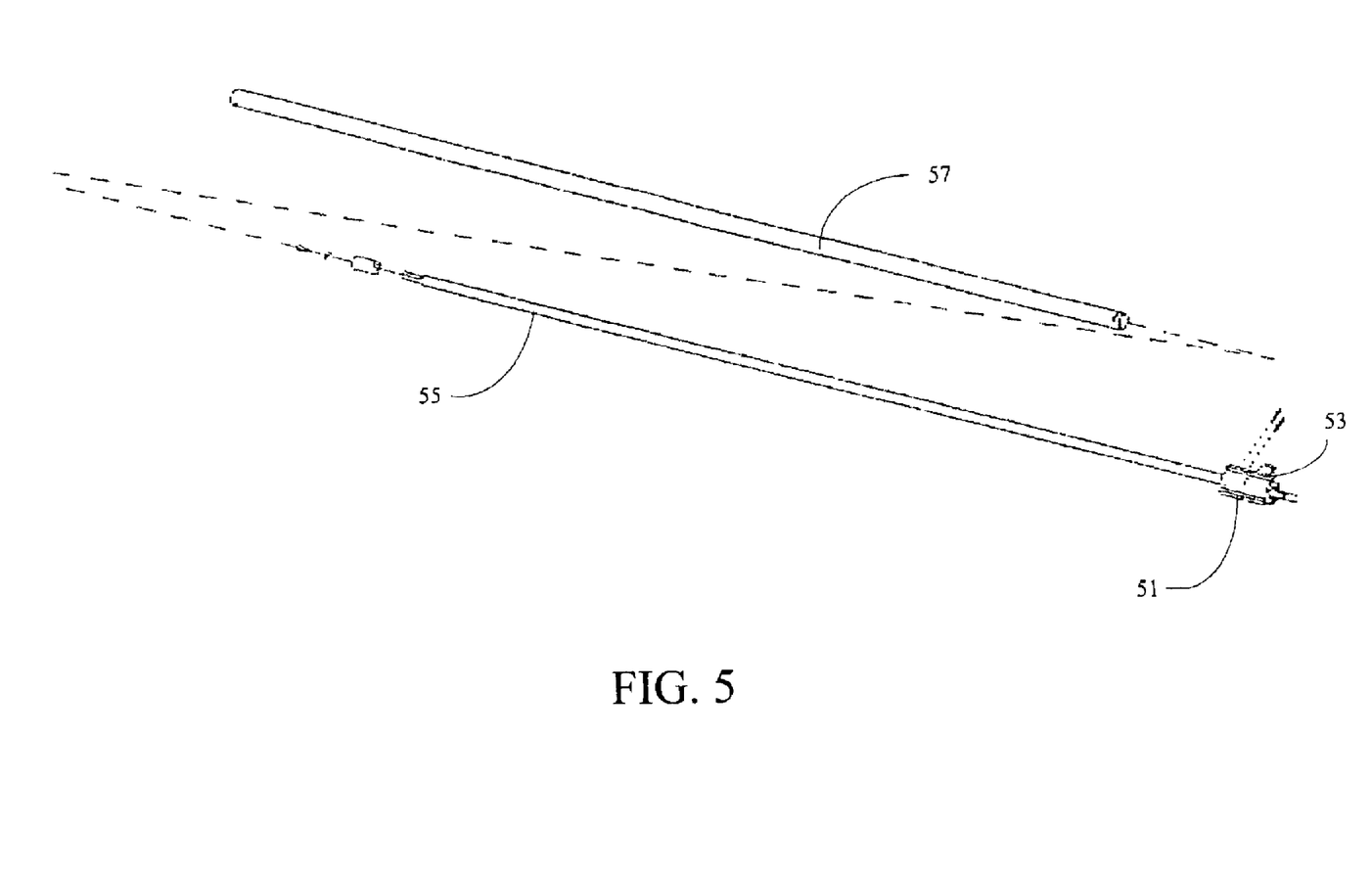
FIG. 5 is a perspective view of a portion of a partially disassembled pole assembly for an apparatus for use in ophthalmic surgery.

As shown in FIG. 5, a magnet 53, such as the magnet shown in FIG. 4, is assembled with or embedded in a moveable element 51, such as a carrier nut. The moveable element is coupled to a lead screw, 55. The lead screw is coupled to apportion of the pole 57. As such, the carrier nut and the associated magnet moves as the lead screw moves. Thus, in one embodiment, the motor 31 (FIG. 3) moves or rotates the lead screw 55 which moves the carrier nut with the magnet and the pole. In turn, the position of the container, supported by the pole, moves correspondingly.

Figure 6:
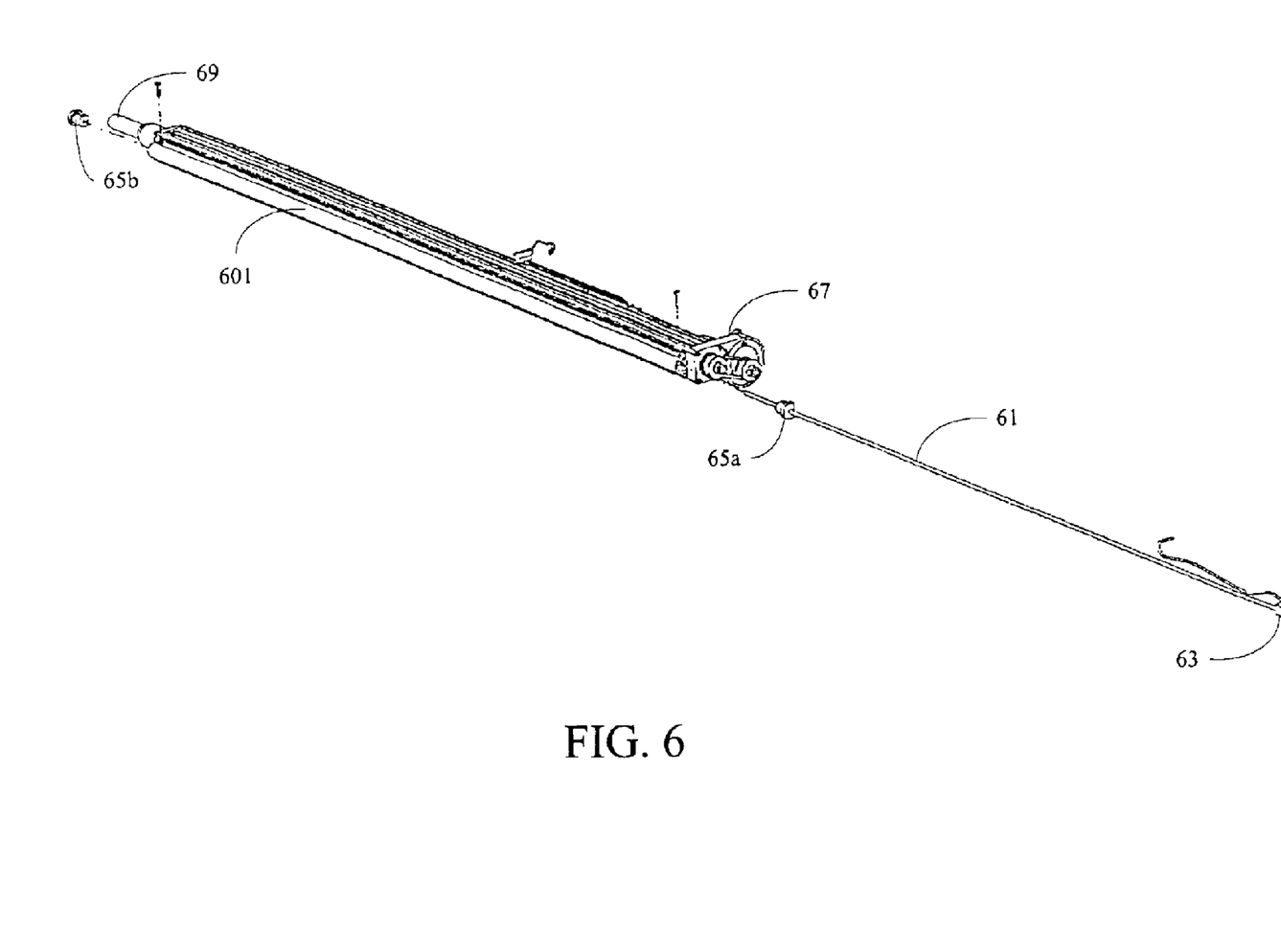
FIG. 6 is a perspective view of portions of a partially disassembled apparatus for use in ophthalmic surgery.

The magnet 53, shown in FIG. 5, and other associated components, including motor 67 and portions of the pole 69, in FIG. 6, are shown assembled in a support structure or assembly 601. A waveguide 61 is coupled on one end to a detector head 63 and threaded through a clamp 65a until the detector head is seated next to the clamp. The waveguide is also inserted into the support assembly and threaded through the magnet (not shown) in the assembly. Another clamp 65b is coupled to the other end of the waveguide, opposite of the detector head. The clamps 65a,b couple the waveguide to the support assembly to keep the waveguide and detector head substantially stationary.

Figure 7:
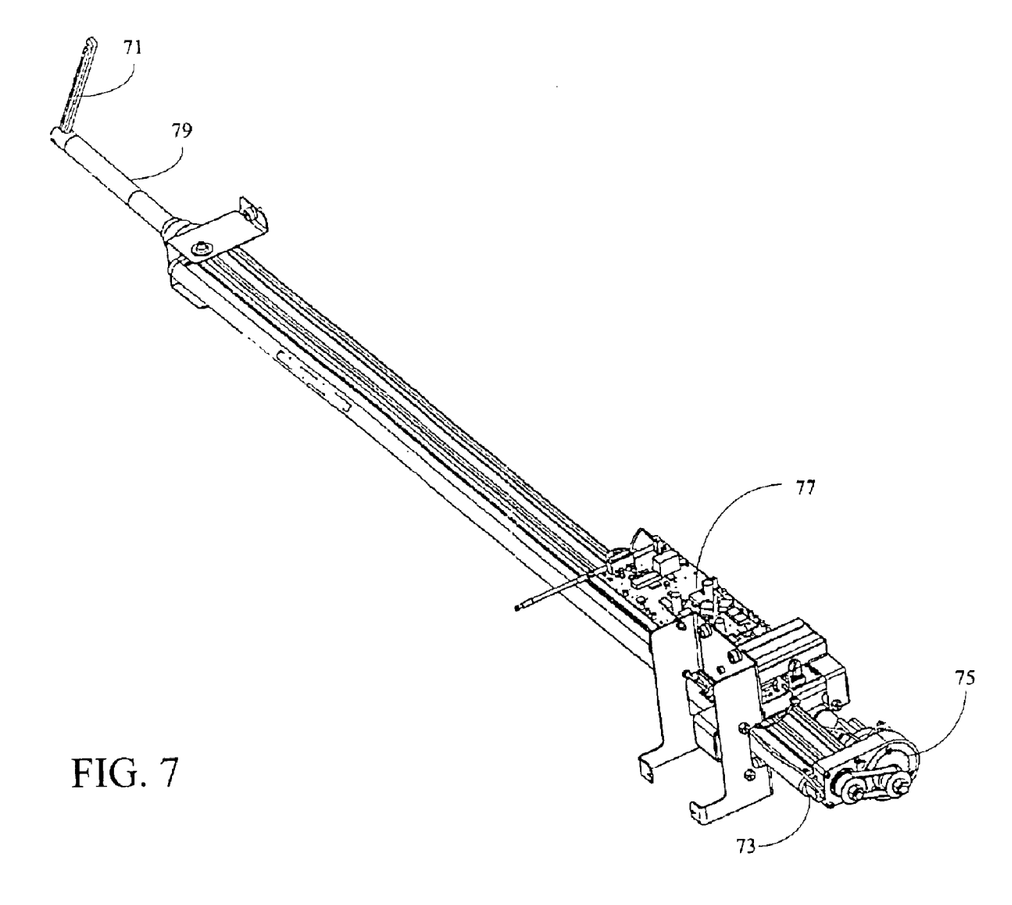
FIG. 7 is a perspective view of an apparatus for use in ophthalmic surgery.

FIG. 7 illustrates an apparatus for use in ophthalmic surgery to supply liquid from a container for the liquid. The apparatus includes a detector head 73, a motor 75 and a controller 77. A magnet, waveguide and carrier nut are also included but are not visible. Additionally, a bottle hanger 71 extends from a pole 79 and suspends a bottle of fluid (not shown) for delivery to a patient's eye.

As such, in the embodiments shown, the detector head 73 generates an interrogating current pulse through the waveguide (not shown). As a result, a magnetic field is generated and propagated along the waveguide. In one embodiment, the waveguide contains a magnetostrictive strain material. The magnet (not shown) also generates a magnetic field. The interaction with the two magnetic fields results in a strain pulse that is sensed by the detector head 73.

Based on the amount time from the generating the current pulse and receiving of the strain pulse, a detector controller (not shown) is able to determine the distance between the magnet and the detector head element.

In one embodiment, the detector controller (not shown) includes a pulse width modulator (not shown). The pulse width modulator generates a pulse signal, e.g., a voltage square or rectangular wave, based on the interaction of the two magnetic fields. The pulse signal is provided to the controller 77. The controller 77 measures the pulse width of the pulse signal to determine the absolute position of the magnet relative to the detector head 73. A timer or counter (not shown) is initiated to determine a number of counts starting from one edge of the pulse signal to the next edge of the pulse signal. Based on the number of counts, the height of the pole is calculated or compared to values or calculations stored in a memory (not shown) to convert the number of counts into distance units, such as centimeters. For example, seventeen counts may correspond to one centimeter. Thus, if the controller 77 determines that the pulse width is fifty counts long, then the pole 17 is about three centimeters away from a predetermined location. The predetermined location may be the location of detector head 73 or an offset, such as a particular zero position or set position, e.g., the location of clamp 65b (FIG. 6). Also, since the magnet (not shown) correspondingly moves with the pole 79, the absolute position of the magnet corresponds to or, in one embodiment, is proportional to the current length of the pole.

Therefore, the controller 77 in conjunction with the positional information provided by the detector controller causes the motor 75 to move the pole 79 in a particular direction and for a specific distance. Although the detector controller and the controller are described as separate units, both units may be provided as a single controller.

Figure 8:
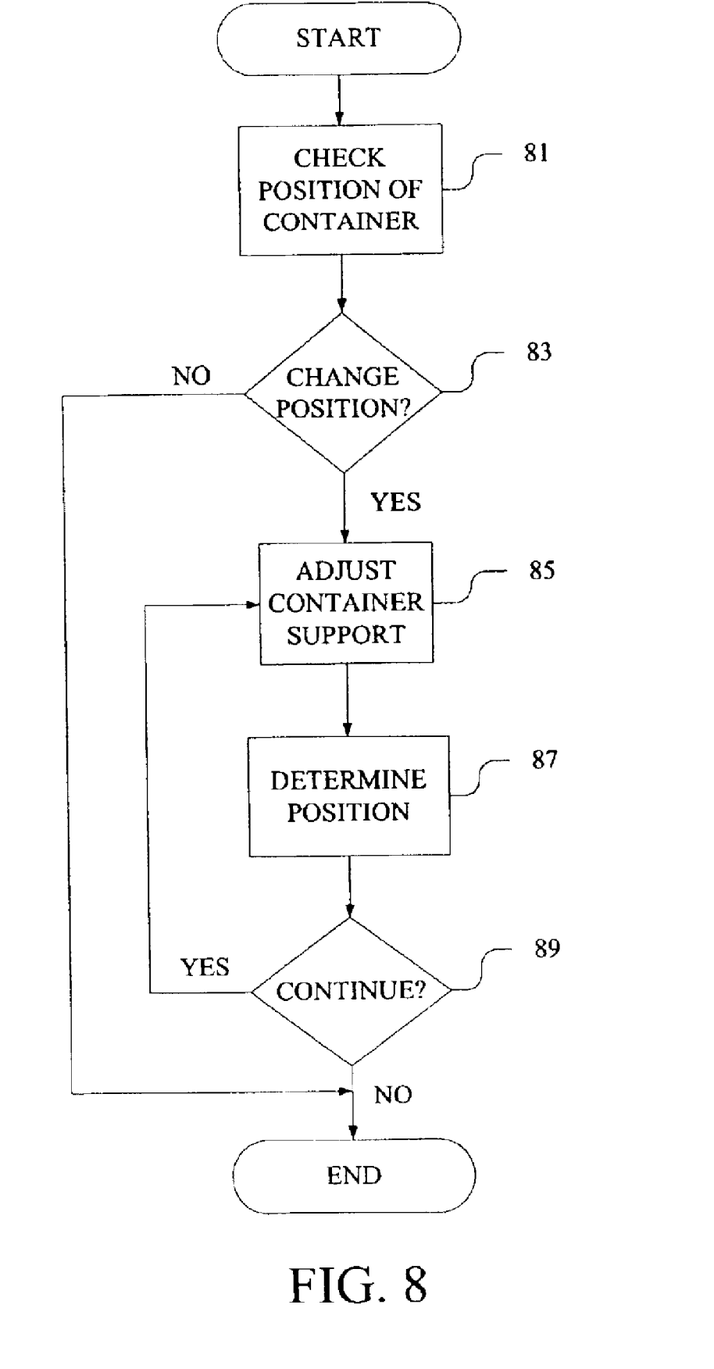
FIG. 8 is a flow diagram of a process of delivering fluid for medical treatment.

In FIG. 8, a process of providing liquid to a patient is diagramed. In block 81, the process determines or checks the height of a container. In one embodiment, a control unit starts an initialization process by causing strain pulse to be generated, measures the absolute position of the position of the container and displays the position to a user via a console display. In block 83, the process determines if the position of the container is to be modified. The user or system determines or provides input for a desired height of the container or a desired amount or flow rate of liquid. If it is determined that the position of container is to be adjusted, the process continues to block 85. Otherwise, the process returns or ends.

In block 85 the process adjusts a structure, e.g., the pole and/or a support structure, supporting the container. In block 87, the process determines the position of the container. In one embodiment this is accomplished in the manner of the determination made in block 81. In block 89, the process determines if the position of the structure is correct, i.e., if the container is at the position desired by the system or user. If so the process ends or returns. Otherwise, the process returns to block 85 to continue to adjust the structure. In one aspect, the process also continually repeats and ends or returns when externally commanded or interrupted. In one embodiment, the process continuously monitors the position of the container to test for faults, e.g., the container is moving when it should be stationary.

The amount of liquid (intraocular or intravenous liquid) flowing is maintained or regulated by the adjustment of the height of the container or a structure, e.g., a pole and/or a support structure, supporting the container. For instance, the container, from which liquid is supplied, is raised or positioned higher than a predetermined position to increase the flow of the liquid. Alternatively, the container, from which the liquid is supplied, can be positioned lower relative to a predetermined position to decrease the flow of the liquid. As such, the process continuously monitors the height of the pole and automatically adjusts the height of the pole to maintain a constant flow of liquid to a patient.

Figure 9:
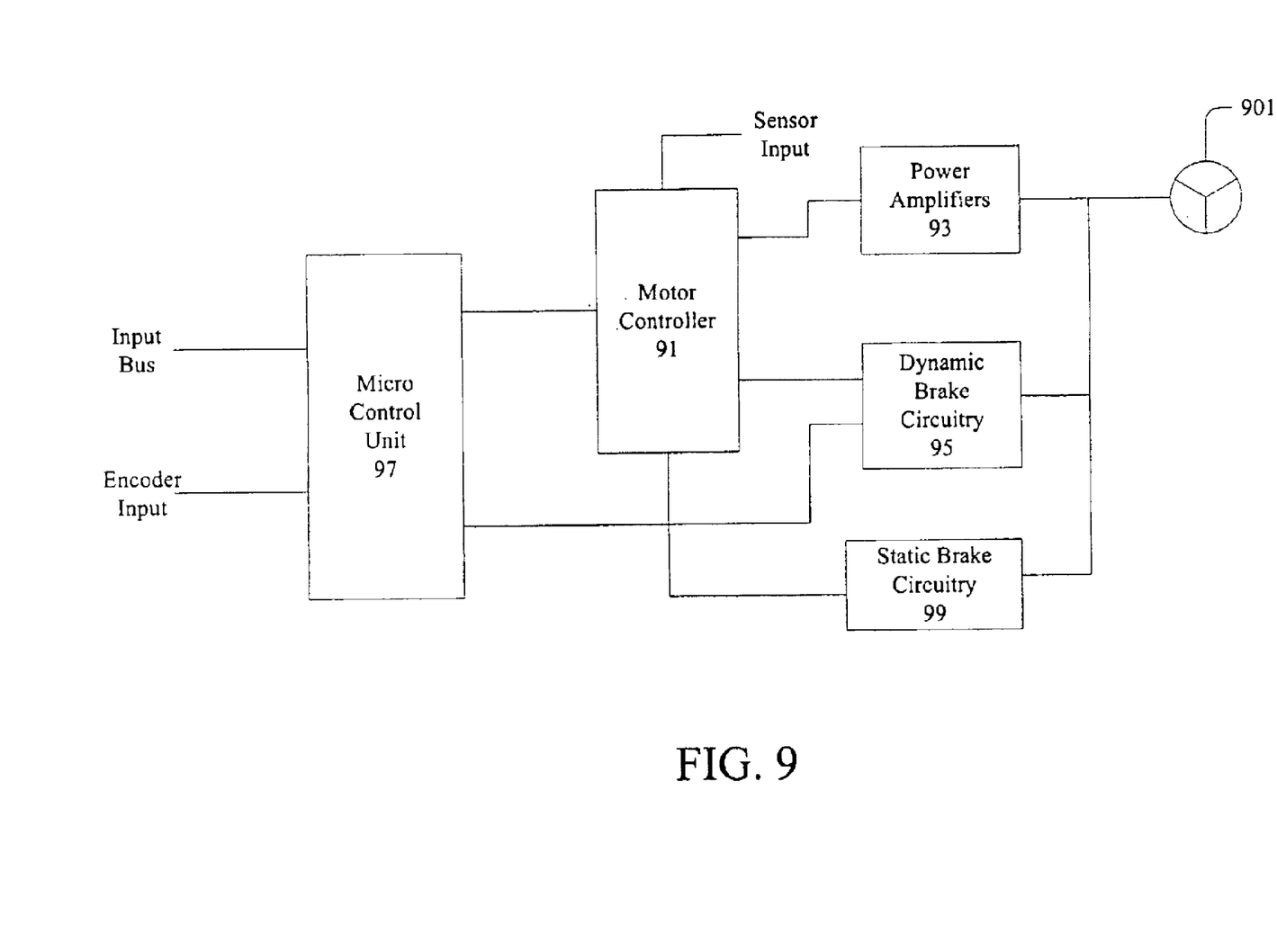
FIG. 9 is a block diagram of one embodiment of a control system to operate a motor.

FIG. 9 illustrates other aspects of the invention. In FIG. 9, a motor controller 91 is coupled to motor sensors (not shown) and power amplifiers 93. The power amplifiers provide phase power to a motor 901. The motor sensors, such as hall effect sensors, provide positional information regarding the motion or rotation of the motor 901. The motor controller 91, in one embodiment, causes DC power to be supplied to the power amplifiers 93 to energize or operate the motor 901 based on the positional information provided or detected by the motor sensors. For example, the motor sensors provide feedback to the motor controller to determine if the motor requires more or less power to rotate a specific or desired number of turns.

The motor controller 91 is also coupled to dynamic brake circuitry 95. The dynamic brake circuitry receives signal input from the motor controller and a micro control unit 97. As such, in cooperation or individually, the motor controller and/or the control unit is able to activate or affect the dynamic brake circuitry. Although the motor controller 91 and the micro control unit 97 are described and shown separately, the motor controller 91 and micro control unit 97 may be a single unit.

The dynamic brake circuitry 95 is also coupled to the motor 901. Thus, based on enable or command signals from the motor controller 91 or micro control unit 97, the dynamic brake circuitry 95 is configured to energize or cause the motor to operate. In one embodiment, the dynamic brake circuitry 95 causes the motor 901 to turn or exert force to prevent movement of a pole (not shown) or other components coupled to the motor 901 and the pole.

In one embodiment, the micro control unit 97 receives an external input from an input bus, such as a CAN bus, and a detector 13/sensor 7 (FIG. 1), such as an absolute encoder. Based on input from the input bus, the micro control unit is configured to cause the motor 901 to move or rotate for a particular number of turns and/or time to adjust a pole or components associated with the pole. The detector/sensor (not shown) provides absolute position information regarding, for example, the height or vertical displacement of a pole. Thus, the micro control 97 can continually cause the motor to rotate until the desired extension of the pole is detected by the detector/sensor. Once the desired position is achieved, the micro control unit 97 is configured to command or otherwise cause the motor controller 91 to stop the motor 901.

Accordingly, based on input from the detector/sensor, the micro control unit can activate the dynamic brake circuitry 95. For example, if the micro control unit 97 determines that the pole has reached a desired height and/or the micro control unit has commanded the motor 901 to stop, any change in position as reported or detected by the detector/sensor indicates that the motor and/or pole is moving. Thus, the dynamic brake circuitry can be activated to maintain a particular position or prevent a change in a particular position and maintain a desired fluid pressure, if any.

A static brake circuitry 99 is also coupled to the motor 901 and a power source or input (not shown). The supplied power can be used to energize the motor. The static brake circuitry detects or senses when power to the motor 901 is removed or lost. As such, in response to power being removed or lost, the static brake circuitry 99 causes the motor to resist movement by shorting one or more windings of the motor. By shorting windings of the motor, an electro motive force is generated by the motor to resist or prevent movement of a pole or other components coupled to the motor and/or the pole.

In one embodiment, a mechanical brake (not shown) is also provided. The mechanical brake is coupled to the motor 901 and/or pole (not shown) and a power source or input (not shown). The power source or input can be the same power source or input supplying power to energize the motor. When power is removed or lost, the mechanical brake is activated to stop or prevent movement of the motor and/or pole. As such, in one embodiment, the pulleys, rotors or other components of the motor 901 or pole are impeded by clamping components together, such as clamping movable components to stationary components. A means for preventing movement of a support can be dynamic brake circuitry, static brake circuitry, and a mechanical brake.

Figure 10:
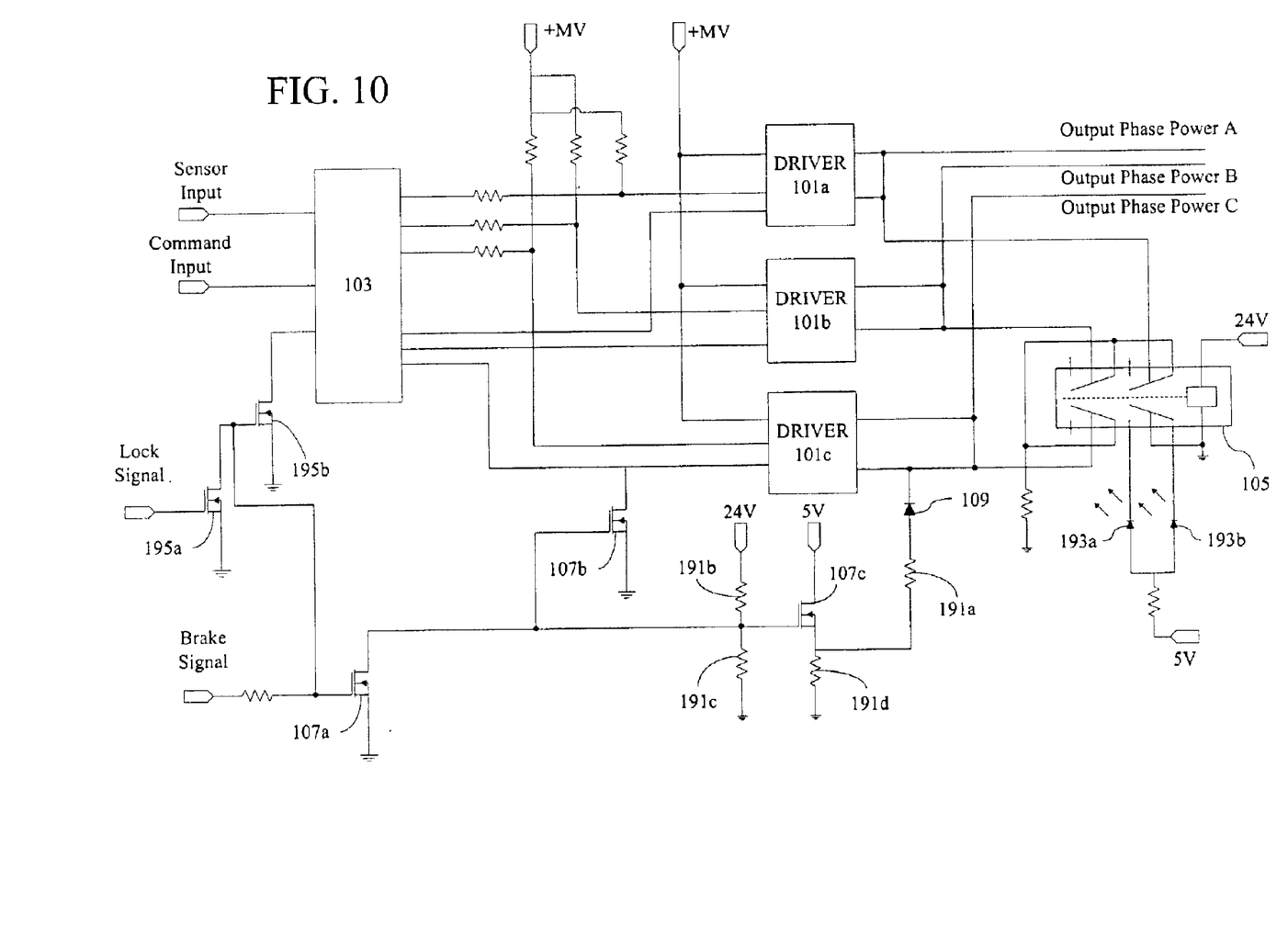
FIG. 10 is a schematic diagram of circuitry used to cause a motor to move and stop.

FIG. 10 is a schematic diagram of circuitry to actuate and prevent actuation of a motor coupled to a pole, which can be a means for moving a support of a container and a means for supplying current to prevent movement of the support of a container. Power amplifiers or drivers 101a–c provide drive currents to the motor, such as a three phase brushless DC motor (not shown). In one embodiment, the motor contains windings and hail effect sensors that, when energized, causes the motor to rotate. A motor controller 103 is also coupled to the drivers 101a–c. The controller receives input from the sensors and input from a micro control unit (not shown) which provides commands or input to the controller, for example, to actuate the motor at a particular rate or speed. In response, the, controller 103 generates drive signals that cause the drivers 101a–c to supply current to the motor to cause the motor to rotate in a particular direction and velocity, e.g., by varying the amplitude and phase of the drive currents supplied to the motor. As a result, a pole (not shown) coupled to the motor (not shown) correspondingly extends or retracts at a particular rate. Likewise, the motor can be commanded or controlled to maintain a particular position or prevent any change in position.

Accordingly, for a three phase motor, the drivers 101a–c provide push/pull drive signals that source or sink motor drive currents to rotate the motor. In addition, driver 101c provides a tri-state drive signal. In various other embodiments, the motor is a single phase motor or another type of multi-phase motor. Power is supplied to each driver from a DC to DC converter (not shown). In one embodiment, the drivers are complementary, N-type and P-type, metal-oxide-silicon (NMOS and PMOS) switches or transistors.

The drivers 101a–c are also separately coupled to a relay 105. The relay is coupled to a power supply or power supply input to monitor whether power is being supplied. As such, under operating conditions, the relay is opened as it is energized by the supplied power. The relay is also coupled to ground separately at each corresponding point where power or each driver is coupled to the relay 105. Thus, in the event that power is lost, the relay closes and paths to ground are opened. As such, phase power is not supplied by the drivers 101a–c to the motor and at least one winding of the motor coupled to the drivers is shorted. With one or more windings of the motor shorted and force or gravity being exerted by the pole coupled to the motor, the motor generates an electromotive force that resists movement of the motor and thus the pole remains stationary. In one embodiment, friction due to the coupling of the pole and motor and other components also assist in preventing adjustment of the pole.

The controller 103 is also coupled to a drain of a transistor 195b. The transistor 195b is gate coupled to the drain of transistor 195a. The transistors 195a,b are each source coupled to ground. The transistors act as switches that turn on based on their gate input. Transistor 195a receives a lock signal via its gate. The lock signal is an overriding or master signal to ensure the motor 901 (FIG. 9) is prevented from rotating, i.e., braking is established. In one embodiment, the lock signal is asserted to identify a fault or error condition. Under normal operations, the lock signal is not asserted. As input from the lock control input is in a particular state, e.g., high, or in another embodiment, low, transistor 195a turns, on and in turn transistor 195b turns off. The transistor 195b causes the controller-to initiate braking. As a result, the controller generates brake signals to prevent the drivers 101a–c from generating, drive currents to the motor. In one embodiment, the controller tri-states the top PMOS transistors of the drivers 101a–c which also shorts the bottom NMOS transistors to short the motor windings to ground.

Transistor 107a is gate coupled to the drain of transistor 195a. The transistor 107a is also source coupled to ground and the drain of the transistor is coupled to the gates of transistors 107b and 107c. The transistors 107b and 107c are similarly coupled as transistor 107a. However, transistor 107b is drain coupled to an input of driver 101c. Transistor 107c is source coupled to an output of driver 101c via diode 109 and resistor 191a. The transistors function as switches that turn on based on their gate input. As such, based on the state of transistor 195a, the transistor 107a turns on or off. For example, when transistor 195a is on, transistor 107a turns off. Subsequently, transistor 107b turns on and transistor 107c turns on. The transistor 107b ensures deactivation of the driver 101c. In addition, transistor 107c is coupled to resistors 191b–d that are supplied differing voltage inputs. As a result, transistor 107c couples a five voltage input to the motor via resistor 191a and diode 109a and thus supplies a holding current to the motor that resists rotation of the motor and/or height adjustment of a pole (not shown) coupled to the motor. In one embodiment, the current supplied is proportional to the force applied to the motor.

Transistor 107a is also gate coupled to a brake control input. In one embodiment, the lock signal is low. As such, transistor 195a is off. As input from the brake control input is in a particular state, e.g., high, or in another embodiment, low, the braking operation is controlled. For example, when the brake control signal is low or not asserted, braking circuitry is applied. As such, transistor 195b and 107a are turned off. Subsequently, transistors 107b and 107c are turned on. Thus, as described above, transistor 107b ensures the deactivation of driver 101c and a holding current is applied to the motor via transistor 107c. Likewise, when the brake control signal is high, braking circuitry is deactivated. As such, transistor 195b and 107a are turned on. Subsequently, transistors 107b and 107c are turned off. Thus, the holding current via transistor 107c is removed or not applied and transistor 107b does not effect the operation of driver 101c.

In one embodiment, the transistors described above are N-type field effect transistors. Other types of transistors may be utilized with a modification in the wiring or coupling of the transistors to various other components, inputs and itself. In other embodiments, other similarly coupled transistors are provided and coupled to the transistors 107a–c, to provide additional control input to active the braking of the motor. In another aspect of the invention, light emitting diodes, such as diodes 193a,b, are coupled to the relay and/or transistors to provide status information, such as indicating that the relay is open or closed.

Figure 11:
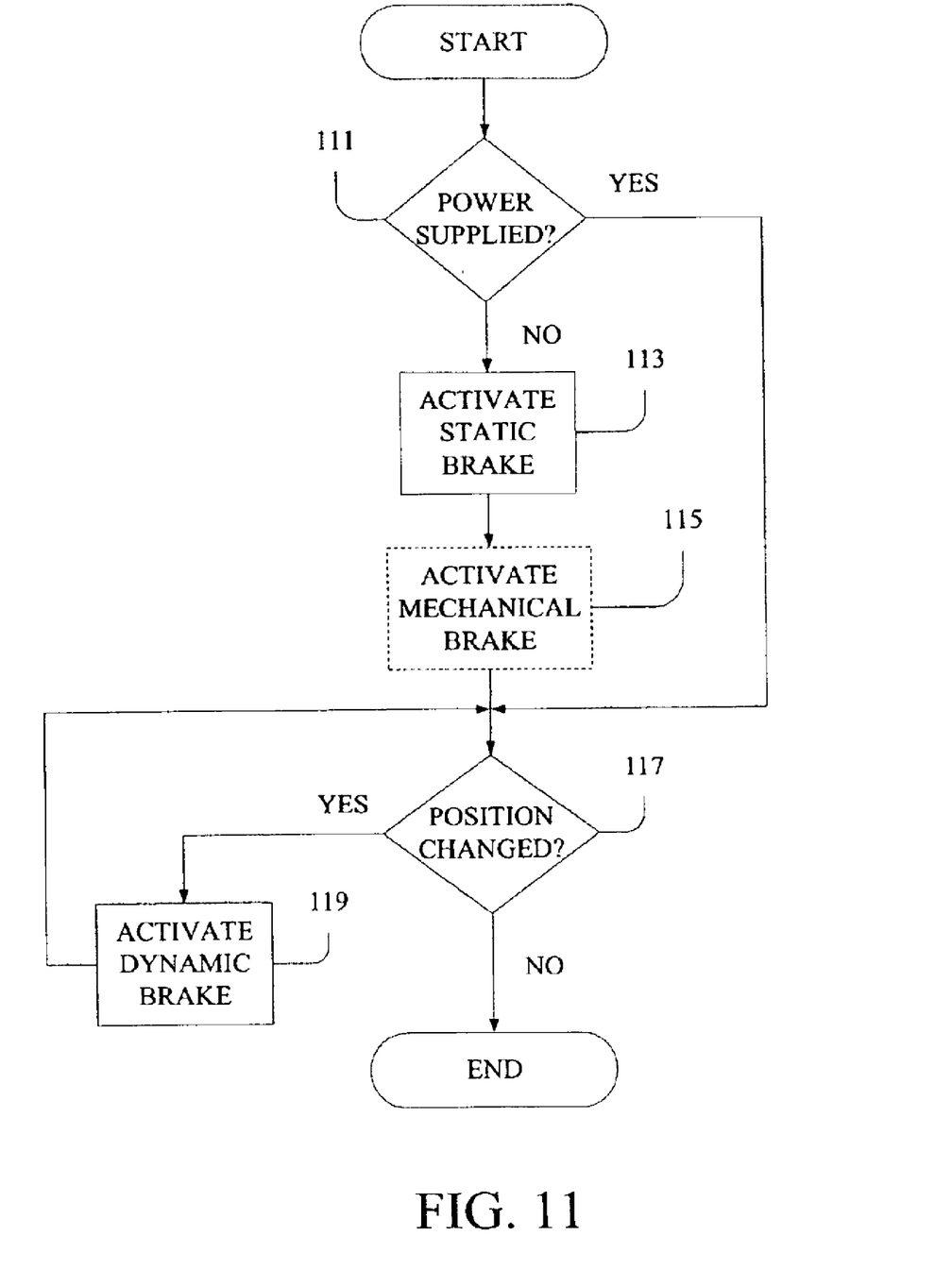
FIG. 11 is a flow diagram of a process of operating a motor for an apparatus for use in ophthalmic surgery.

In FIG. 11, a process of preventing movement of a pole or support used to supply liquid to a patient is diagramed. In block 111, the process determines or checks whether power is being supplied or is lost. In one embodiment, a relay is tripped to indicate that power is lost. In another embodiment, the process is notified from an external source that power is about to be lost, i.e., the system is to be shutdown. If the process determines that power is lost or will be lost, the process activates static braking to prevent movement of the pole in block 113. In one aspect, a mechanical brake is also activate in block 115. If the process determines that power is not lost, the process continues to block 117.

In block 117, the process determines the position or a change in position of the pole. In one embodiment, the process reads or is provided the absolute position information of the pole or container coupled to the pole from an encoder, e.g., detector 13 and sensor 7 (FIG. 1). If the process determines that the position of the pole has changed or is not a expected position, the process, in block 119, activates a dynamic braking to adjust the pole to place the pole at the expected position or to prevent any change in position. The process repeats to block 117 to check again the position of the pole. In one embodiment, the process continues back to block 111 to check again if power is being supplied. If the process determines that the position of the pole has not changed or is as expected, the process ends or returns. In one aspect, the process continually repeats and ends or returns when externally commanded or interrupted.

Thus, the present invention provides methods and apparatus for use in ophthalmic surgery. Although this invention has been described in relation to certain specific embodiments, many additional modifications and variations will be apparent to those skilled in the art. It is, therefore, to be understood that this invention may be practiced otherwise than as specifically described. Thus, the present embodiments of the present invention should be considered in all respects as illustrative and not restrictive. The scope of the invention is to be determined by the appended claims, and their equivalents rather than the foregoing description.

We claim:

1. An apparatus for use in surgery in which a container for fluid is connected to a line through which fluid flows to a surgical handpiece for the irrigation of a patient's eye, the apparatus comprising:
   a) a base;
   b) a support extending from the base and coupled to the container from which fluid is supplied to the surgical handpiece;
   c) an encoder arranged to determine the absolute position of the support, the encoder including a sensor and a detector, the absolute position being the distance between the encoder and the detector along the support; and
   d) a controller arranged to adjust the height of the support based on the absolute position determined.

2. The apparatus of claim 1 further comprising a motor arranged to move the support along an axis.

3. The apparatus of claim 2 wherein the controller is arranged to cause the motor to move the support.

4. The apparatus of claim 1 wherein the encoder comprises:
   a) a sensor coupled to a portion of the support and arranged to emit a first magnetic field; and
   b) a detector arranged to emit a second magnetic field and to detect an indication of an interaction of the first and second magnetic fields.

5. The apparatus of claim 4 wherein the controller is arranged to determine the distance between the detector and the sensor based on a determination of the time between emission of the second magnetic field and detection of the indication of the interaction of the first and second magnetic fields.

6. The apparatus of claim 5 wherein the detector comprises a signal conditioner and a waveguide.

7. The apparatus of claim 6 wherein the signal conditioner generates a signal and the controller determines the height of the support based on a pulse width of the signal.

8. The apparatus of claim 7 wherein the signal conditioner causes current to flow through the waveguide.

9. The apparatus of claim 6 wherein the sensor comprises a magnetic element substantially surrounding the waveguide.

10. The apparatus of claim 4 wherein the detector is arranged to supply a current, the current causing the second magnetic field to be emitted.

11. The apparatus of claim 10 wherein the detector is arranged to detect a pulse emitted from the interaction of the first magnetic field and the second magnetic field.

12. The apparatus of claim 11 wherein the controller is arranged to determine the position of the sensor based on a determination of the time between emission of the second magnetic field and detection of the pulse.

13. The apparatus of claim 11 wherein the controller is arranged to determine the height of the support based on a determination of the time between emission of the second magnetic field and detection of the pulse.

14. The apparatus of claim 11 further comprising a carrier coupled to the sensor and arranged to travel along a portion of the support.

15. The apparatus of claim 14 further comprising a motor arranged to move the carrier along the portion of the support.

16. The apparatus of claim 15 wherein the controller is arranged to cause the motor to move the carrier in a desired direction for a desired distance.

17. The apparatus of claim 1 further comprising circuitry arranged to prevent movement of the support and wherein the controller is arranged to energize the circuitry based on the absolute position determined.

18. The apparatus of claim 1, wherein the absolute position is defined relative to a distance between two points on the support.

19. The apparatus of claim 18, wherein a first point is fixed, and a second point is variable.

20. The apparatus of claim 18, wherein the absolute position is determined without determining a previous location of the support.

21. The apparatus of claim 1, the detector being fixed in position relative to the base.

22. The apparatus of claim 1, the sensor being fixed in position relative to the support.

23. The apparatus of claim 1, the absolute position being determined without determining a previous location of the pole.

24. An apparatus for use in ophthalmic surgery in which a container for fluid is connected to a line through which fluid flows to a surgical handpiece for the irrigation of a patient's eye, the apparatus comprising:

a) a support coupled to the container from which fluid is supplied to the surgical handpiece;

b) a motor arranged to generate an electro motive force; and c) circuitry arranged to prevent vertical movement of the support based on the electro motive force generated, the circuitry causing at least one winding of the motor to be shorted.

25. An apparatus for use in ophthalmic surgery in which a container for fluid is connected to a line through which fluid flows to a surgical handpiece for the irrigation of a patient's eye, the apparatus comprising:

a) a support coupled to the container from which fluid is supplied to the surgical handpiece;

b) a motor arranged to generate an electro motive force; and c) circuitry comprising a relay and drivers that supply power to the motor, the relay coupled to the drivers, the circuitry arranged to prevent vertical movement of the support based on the electro motive force generated.

26. The apparatus of claim 25 wherein the relay has an active state and an inactive state.

27. The apparatus of claim 26 wherein the relay, in an active state, allows power to be supplied to the motor and, in an inactive state, prevents power from being supplied to the motor.

28. The apparatus of claim 26 wherein the relay changes state based on whether power is being supplied to the relay.

29. An apparatus for use in ophthalmic surgery in which a container for fluid is connected to a line through which fluid flows to a surgical handpiece for the irrigation of a patient's eye, the apparatus comprising:

a) a pole;

b) a magnet for emitting a first magnetic field;

c) a carrier housing the magnet and coupled to a portion of the support;

d) a waveguide proximate the pole, the waveguide including magnetostrictive strain material;

e) a signal conditioner arranged to cause current to flow through the waveguide to emit a second magnetic field and further arranged to detect a pulse generated from an interaction of the first magnetic field and a second magnetic field;

f) a motor having windings and arranged to adjust the position of the pole and the carrier;

g) a control board arranged to determine the height of the pole based on a time interval between the flow of current to the detection of the pulse by the signal conditioner and further arranged to energize the motor to adjust the height of the pole;

h) transistor, drivers arranged to supply drive currents to the windings of the motor; and i) transistor switches arranged to deactivate the drivers and to supply a current to one of the windings to prevent movement of the motor.

30. A method for use in ophthalmic surgery in which a container for fluid is connected to a line through which fluid flows to a surgical handpiece for the irrigation of a patient's eye, the method comprising the steps of:

a) attaching to a support the container from which fluid is supplied to the surgical handpiece;

b) detecting the absolute position of the support with reference to a base, the step of detecting the absolute position comprising:

i) emitting, a first magnetic field proximate the support; and ii) emitting a second magnetic field along a waveguide to interact with the first magnetic field; and c) adjusting the height of the support based on the absolute position detected.

31. The method of claim 30 further comprising generating a pulse in response to the interaction of the first and second magnetic fields.

32. The method of claim 31 further comprising measuring an amount of time the pulse takes to reach a predetermined location.

33. The method of claim 32 wherein the step of detecting the absolute position of the support is based on a time interval between when the second magnetic field is emitted to when the pulse reaches a predetermined location.

34. The method of claim 33 further comprising preventing change of position of the support based on the absolute position detected.

35. A method for use in ophthalmic surgery in which a container for fluid is connected to a line through which fluid flows to a surgical handpiece for the irrigation of a patient's eye, the method comprising the steps of a) attaching to a support the container from which fluid is supplied to the surgical handpiece;

b) generating an electro motive force;

c) preventing chance of height of the support based on the electro motive force generated;

d) detecting a change in power and generating the electro motive force based on the chance in power detected; and e) shorting at least one winding of the motor.

36. An apparatus for use in surgery in which a container for fluid is connected to a line through which fluid flows to a surgical handpiece for the irrigation of a patient's eye, the apparatus comprising:

a) a base;

b) a support extending from the base and coupled ) to the container from which fluid is supplied to the surgical handpiece;

c) an encoder arranged to determine the absolute position of the support, wherein the encoder comprises
a sensor coupled to a portion of the support and arranged to emit a first magnetic field; and
a detector arranged to emit a second magnetic field and to detect an indication of an interaction of the first and second magnetic fields; and d) a controller arranged to adjust the height of the support based on the absolute position determined.

37. An apparatus for use in ophthalmic surgery in which a container for fluid is connected to a line through which fluid flows to a surgical handpiece for the irrigation of a patient's eye, the apparatus comprising:

a) a means for supporting the container from which fluid is supplied to the surgical handpiece;

b) a means for determining the absolute position of the means for supporting the container with reference to a base, wherein the means for determining the absolute position comprises:
a means for emitting a first magnetic field proximate the support means, and
a means for emitting a second magnetic field to interact with the first magnetic field; and c) a means for adjusting the height of the support based on the absolute position determined.

38. An apparatus for use in ophthalmic surgery in which a container for fluid is connected to a line through which fluid flows to a surgical handpiece for the irrigation of a patient's eye, the apparatus comprising:
   a) a support coupled to the container from which fluid is supplied to the surgical handpiece;
   b) a motor arranged to generate an electro motive force; and
   c) circuitry arranged to prevent vertical movement of the support based on the electro motive force generated, wherein the circuitry causes at least one winding of the motor to be shorted.

39. An apparatus for use in ophthalmic surgery in which a container for fluid is connected to a line through which fluid flows to a surgical handpiece for the irrigation of a patient's eye, the apparatus comprising:
   a) a support coupled to the container from which fluid is supplied to the surgical handpiece;
   b) a motor arranged to generate an electro motive force; and
   c) circuitry arranged to prevent vertical movement of the support based on the electro motive force generated, wherein the circuitry comprises a relay and drivers that supply power to the motor, the relay coupled to the drivers.

40. A method for use in ophthalmic surgery in which a container for fluid is connected to a line through which fluid flows to a surgical handpiece for the irrigation of a patient's eye, the method comprising the steps of:
   a) attaching to a support the container from which fluid is supplied to the surgical handpiece;
   b) detecting the absolute position of the support with reference to a base, wherein the step of detecting the absolute position comprises:
   emitting, a first magnetic field proximate the support, and
   emitting a second magnetic field along a waveguide to interact with the first magnetic field; and
   c) adjusting the height of the support based on the absolute position detected.

* * * * *